(12) United States Patent
Weber et al.

(10) Patent No.: US 8,353,944 B2
(45) Date of Patent: Jan. 15, 2013

(54) BIFURCATION DELIVERY SYSTEM

(75) Inventors: Jan Weber, Maple Grove, MN (US);
Karl A. Jagger, Deephaven, MN (US);
Tracee Eidenschink, Wayzata, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1550 days.

(21) Appl. No.: 11/079,756

(22) Filed: Mar. 14, 2005

(65) Prior Publication Data
US 2006/0206188 A1 Sep. 14, 2006

(51) Int. Cl.
*A61F 2/06* (2006.01)
(52) U.S. Cl. ...................................................... 623/1.11
(58) Field of Classification Search .................. 623/1.11; 604/533, 535, 530; 285/272, 282
See application file for complete search history.

(56) References Cited

U.S. PATENT DOCUMENTS

| | | | |
|---|---|---|---|
| 4,906,244 A | 3/1990 | Pinchuk et al. | 606/194 |
| 5,397,305 A | 3/1995 | Kawula et al. | |
| 5,500,181 A | 3/1996 | Wang et al. | 264/532 |
| 5,697,948 A * | 12/1997 | Marin et al. | 606/198 |
| 5,749,825 A * | 5/1998 | Fischell et al. | 600/3 |
| 5,855,565 A | 1/1999 | Bar-Cohen et al. | |
| 6,290,673 B1 | 9/2001 | Shanley | 604/102.02 |
| 6,471,672 B1 * | 10/2002 | Brown et al. | 604/101.01 |
| 6,514,237 B1 * | 2/2003 | Maseda | 604/533 |
| 6,540,719 B2 * | 4/2003 | Bigus et al. | 604/96.01 |
| 6,599,315 B2 | 7/2003 | Wilson | 623/1.11 |
| 2001/0037141 A1 * | 11/2001 | Yee et al. | 623/1.11 |
| 2002/0072755 A1 | 6/2002 | Bigus et al. | |
| 2003/0055483 A1 | 3/2003 | Gumm | 623/1.11 |
| 2004/0041395 A1 * | 3/2004 | Frost | 285/98 |
| 2004/0172121 A1 | 9/2004 | Eidenschink et al. | |
| 2005/0187603 A1 | 8/2005 | Eidenschink et al. | |

FOREIGN PATENT DOCUMENTS
WO  WO 03/017872 A1  3/2003

OTHER PUBLICATIONS

BarCohen et al., Electro-Active Polymer Actuators for Planetary Applications, *Proceeding of SPIE Annual International Symposium on Smart Structures and Materials*, Mar. 1999, Paper No. 3669-05, Newport Beach, CA.
U.S. Appl. No. 10/785,449, filed Feb. 24, 2004, Eidenschink.

* cited by examiner

*Primary Examiner* — Katherine Dowe
(74) *Attorney, Agent, or Firm* — Seager, Tufte & Wickhem, LLC

(57) ABSTRACT

A catheter assembly comprises a catheter shaft having a proximal region a distal region and a rotational seal therebetween. The rotational seal comprises a first component fixedly engaged to the proximal region and a second component fixedly engaged to the distal region. The components engaged in an overlapping arrangement. The rotational seal is actuatable between a non-activated and activated states. In the non-activated state the first component and the second component are separated by a gap which provides for the distal region of the catheter shaft to be rotatable relative to the proximal region. In the activated state at least a portion of the first component and the second component being sealingly engaged together such that distal region is made static relative to the proximal region.

16 Claims, 8 Drawing Sheets

BIFURCATION DELIVERY SYSTEM

CROSS-REFERENCE TO RELATED APPLICATIONS

Not Applicable

STATEMENT REGARDING FEDERALLY SPONSORED RESEARCH

Not Applicable

BACKGROUND OF THE INVENTION

Description of the Related Art

Stent delivery systems for deployment of one or more stent bodies at or around a vessel bifurcation have been proposed. Often such stents generally have an opening which allows for unimpeded blood flow into one or more side branch arteries, and/or through which an additional stent body may be deployed. However, problems are still encountered in orienting a stent relative to the side branch at the bifurcation of the primary and secondary passages. Moreover, such bifurcated assemblies are typically specially manufactured at an increased cost over a more standard stent intended for single vessel deployment.

In delivering a stent to a vessel location, many current devices rely on either passive torque (e.g., pushing the stent forward and allowing the stent that is fixed on the guidewire/balloon to passively rotate itself into place) or creating torque from outside of the patient to properly orient the medical device in the passage. Such catheter assemblies include those described in U.S. Pat. No. 5,749,825; U.S. Pat. No. 6,599,315 and U.S. Pat. No. 6,290,673 the entire content of each of which being incorporated herein by reference.

Unfortunately such devices still often require a significant portion of the catheter assembly in addition to the balloon to be subjected to torque in order to align the stent with the side branch opening of the bifurcation. Subjecting the catheter as well as a vessel to such extraneous torque may be considered undesirable.

Thus, a need exists to provide a catheter which is capable of allowing a medical device such as a stent to be easily maneuvered and aligned at a vessel bifurcation or other location without the need to torque or rotate the entire catheter shaft in order to align the stent at a vessel bifurcation. At least one device has been proposed wherein the distal portion of the catheter, including the portion about which the stent is mounted, is configured to be rotatable relative to the rest of the catheter assembly. An example of such a device is described in U.S. patent application Ser. No. 10/226,362, filed Aug. 22, 2002, and published as U.S. Published Application. No. 2003-0055483-A1; the entire contents of which are incorporated herein by reference.

In assemblies having a distal end portion which is freely rotatable it may be desirable to limit or regulate the rotation of the rotatable portion. This can be accomplished by providing a selectively actuated seal or valve in the proximal proximity of the distal end region or balloon, which can be activated to allow or prevent free rotation. Some examples of such regulating mechanisms are described in U.S. patent application Ser. No. 10/785,449, filed Feb. 24, 2004, of which the entire contents are incorporated herein by reference.

Though previously proposed rotation regulating mechanism may be available, it is desirable to provide catheter assemblies with alternative and more optimized configurations.

All U.S. patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

BRIEF SUMMARY OF THE INVENTION

In at least one embodiment, the present invention is directed to a catheter assembly wherein the catheter comprises a distal end region, which may include a balloon, that is independently rotatable relative to the proximal region of the catheter assembly. In some embodiments an expandable stent is disposed about a portion of the distal end region prior to deployment therefrom, In some embodiments, the catheter assembly employs one or more control seals for regulating rotation of the distal end region. In at least one embodiment the control seal(s) is at least partially constructed of one or more ionic polymers or electro-active polymer (EAP) materials.

EAP materials actuate via the reversible counter-ion insertion and expulsion that occurs during redox cycling. Significant volume changes up to 30% occur through oxidation and reduction reactions at corresponding electrodes through exchanges of ions with an electrolyte. Electrodes are commonly fabricated from polypyrrole or polyaniline, or PAN doped with HCl. CP actuators requires voltages in the range of 1-5 V. Variations to the voltage can control actuation speeds. Suitable ionic polymers are polypyrrole, polyethylenedioxythiophene, poly(p-phenylene vinylene)s, polyaniline and polythiophenes.

In some embodiments a catheter assembly is provided wherein a rotation regulating seal is positioned proximal to the catheter balloon or rotatable region. The seal can be configured to allow rotation in the non-pressurized state and to fix the angular relation in a pressurized state.

In at least one embodiment a catheter assembly is provided with an rotation regulating seal in the outer shaft as well as in the inner shaft of the catheter proximal to the balloon.

In at least one embodiment a rotation regulating seal is configured to have two components or bushings: a first or proximal bushing component and a second or distal bushing component. Though portions of the components are longitudinally offset from one another (thus the designators proximal and distal) a portion of one component is disposed about the other in a configuration commonly referred to as a "bayonet" lock, which forms the actual seal mechanism. At least one gap exists between the components when the seal is in the rotatable or non-activated state. In some embodiments, a layer of EAP material is affixed to one or both of the components within the gap, such that when "activated" or exposed to a low voltage electric current the EAP layer expands to close the gap and seal the bushing components against one another, thereby stopping the rotation of the catheter region distal to the seal. In some embodiments, pressurizing the lumen adjacent to the seal will also or alternatively provide for "activation" of the seal.

These and other embodiments which characterize the invention are pointed out with particularity in the claims annexed hereto and forming a part hereof. However, for a better understanding of the invention, its advantages and objectives obtained by its use, reference should be made to the drawings which form a further part hereof and the accompanying descriptive matter, in which there is illustrated and described a embodiments of the invention.

BRIEF DESCRIPTION OF THE SEVERAL VIEWS OF THE DRAWING(S)

A detailed description of the invention is hereafter described with specific reference being made to the drawings.

DETAILED DESCRIPTION OF THE INVENTION

Figure 1:
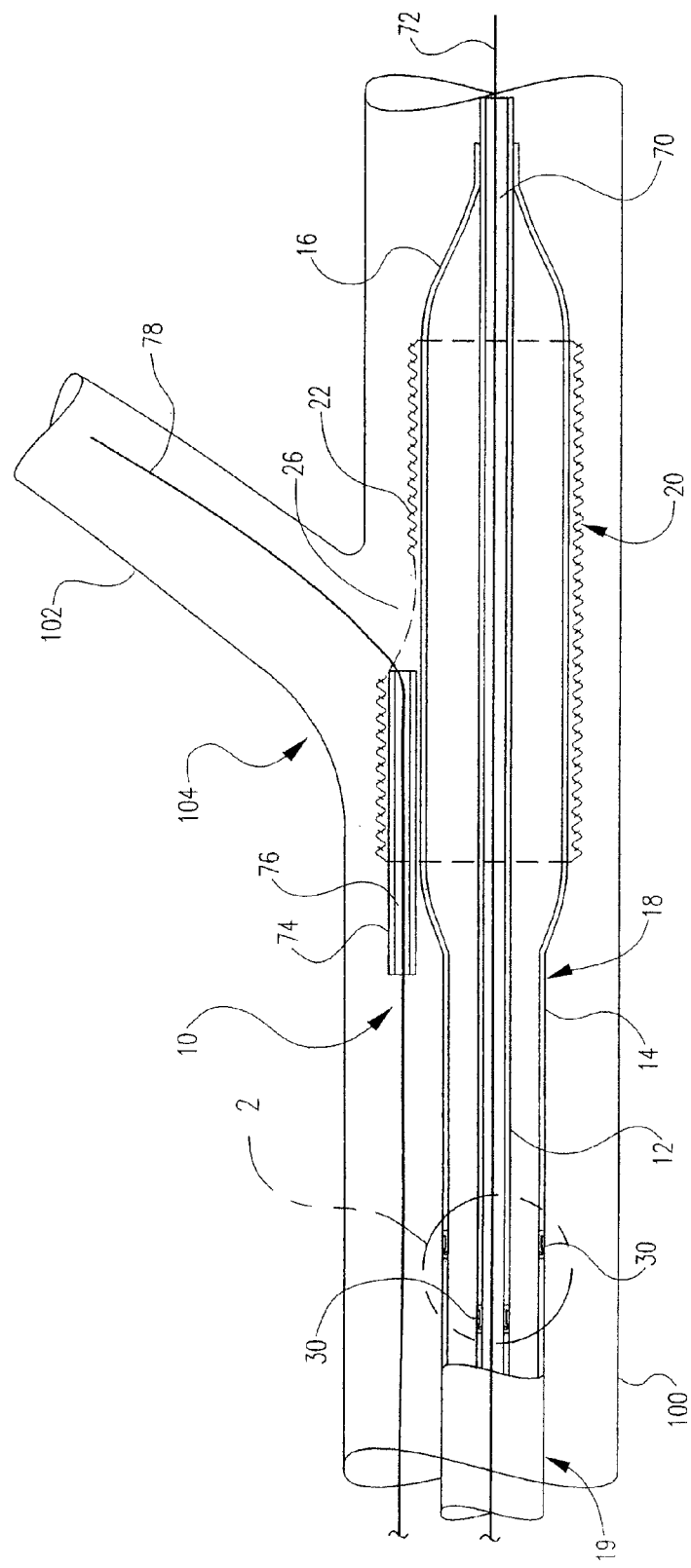
FIG. 1 is a longitudinal side perspective view of an embodiment of the invention shown in the environment of a vessel bifurcation.

While this invention may be embodied in many different forms, there are described in detail herein specific embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

Referring now to the drawings which are for the purposes of illustrating embodiments of the invention only and not for purposes of limiting same, in at least one embodiment of the invention, an example of which is shown in FIG. 1, a catheter assembly 10 comprises an inner catheter shaft 12 and an outer catheter shaft 14. At a distal end region 18 of the assembly 10 an expandable medical balloon 16 is engaged to the shafts 12 and 14.

Balloon 16 may be a typical angioplasty, stent delivery balloon or other inflatable member which may be used or incorporated into a catheter assembly. The balloon 16 may be constructed of any suitable balloon material known to those of skill in the art. Commonly employed materials include the thermoplastic elastomeric and non-elastomeric polymers and the thermosets including the moisture curable polymers.

Examples of suitable materials include but are not limited to, polyolefins, polyesters, polyurethanes, polyamides, polyimides, polycarbonates, polyphenylene sulfides, polyphenylene oxides, polyethers, silicones, polycarbonates, styrenic polymers, copolymers thereof, and mixtures thereof. Some of these classes are available both as thermosets and as thermoplastic polymers. See commonly assigned U.S. Pat. No. 5,500,181, for example, which is incorporated by reference herein in its entirety. As used herein, the term copolymer shall be used to refer to any polymeric material formed from more than one monomer.

As used herein, the term "copolymer" shall be used to refer to any polymer formed from two or more monomers, e.g. 2, 3, 4, 5 and so on and so forth.

Useful polyamides include, but are not limited to, nylon 12, nylon 11, nylon 9, nylon 6/9 and nylon 6/6. The use of such materials is described in U.S. Pat. No. 4,906,244, for example, the entire content of which is incorporated by reference herein in its entirety.

Examples of some copolymers of such materials include the polyether-block-amides, available from Elf Atochem North America in Philadelphia, Pa. under the tradename of PEBAX®. Another suitable copolymer is a polyetheresteramide.

Suitable polyester copolymers, include, for example, polyethyelene terephthalate and polybutylene terephthalate, polyester ethers and polyester elastomer copolymers such as those available from DuPont in Wilmington, Del. under the tradename of HYTREL®.

Block copolymer elastomers such as those copolymers having styrene end blocks, and midblocks formed from butadiene, isoprene, ethylene/butylene, ethylene/propene, and so forth may be employed herein. Other styrenic block copolymers include acrylonitrile-styrene and acrylonitrile-butadiene-styrene block copolymers. Also, block copolymers wherein the particular block copolymer thermoplastic elastomers in which the block copolymer is made up of hard segments of a polyester or polyamide and soft segments of polyether.

Specific examples of polyester/polyether block copolymers are poly(butylene terephthalate)-block-poly(tetramethylene oxide) polymers such as ARNITEL® EM 740, available from DSM Engineering Plastics. and HYTREL® polymers available from DuPont de Nemours & Co, already mentioned above.

The above materials are intended for illustrative purposes only, and not as a limitation on the scope of the present invention. Suitable polymeric materials available for use are vast and too numerous to be listed herein and are known to those of ordinary skill in the art.

In some embodiments the assembly 10 is directed to the delivery of one or more stents, such as for example the stent 20 shown in FIG. 1.

As used herein the term 'stent' refers to an expandable prosthesis for implantation into a body lumen or vessel and includes devices such as stents, grafts, stent-grafts, vena cava filters, expandable frameworks, etc. In some embodiments a stent may be at least partially constructed of any of a variety of materials such as stainless steel, nickel, titanium, nitinol, platinum, gold, chrome, cobalt, as well as any other metals and their combinations or alloys. In some embodiments a stent may be at least partially constructed of a polymer material. In some embodiments a stent may be at least partially constructed of a shape-memory polymer or material. In some embodiments a stent may be balloon expandable, self-expandable, hybrid expandable or a combination thereof. In some embodiments a stent may include one or more radiopaque members. In some embodiments a stent may include one or more therapeutic and/or lubricious coatings applied thereto.

In some embodiments the stent or other portion of the assembly may include one or more areas, bands, coatings, members, etc. that is (are) detectable by imaging modalities such as X-Ray, MRI or ultrasound. In some embodiments at least a portion of the stent and/or adjacent assembly is at least partially radiopaque.

In the embodiment shown in FIG. 1, the assembly 10 is configured to deliver the stent 20 to a bifurcation 104 of vessels, such as the primary vessel 100 and secondary vessel 102 shown. The stent 20 is defined by a stent body or framework 22, the stent body 22 defines a primary passage or lumen 24 through which following delivery of the stent bodily fluids 106 in the primary vessel 100 will be able to flow through, such as in the manner depicted in FIG. 8.

The stent 20 also includes a secondary opening 26 which is defined by the stent body 22, and which is in fluid communication with the primary lumen 24, thereby providing fluid communication between the primary lumen 24 and the secondary vessel 102 following delivery of the stent 20.

As is illustrated in FIG. 1 alignment of the secondary opening 26 of the stent 20 with the secondary vessel 102 is accomplished by rotating only the distal end region 18 of the assembly 10 within the primary vessel 100 rather than the entire assembly 10. In the embodiment shown, rotatability of the distal end region 18 is imparted by providing both the inner shaft 12 and the outer shaft 14 with a seal mechanism 30. The seal mechanisms 30 are configured to regulate rotatability of the distal end region 18, relative to the region of the catheter assembly 10 proximal to the seals 30 (this region hereinafter being referred to as the proximal region 19), such that in a non-activated state the seal(s) 30 permit rotation of the distal end region 18 relative to the proximal region 19 and in the activated state the seal(s) 30 act to seal the proximal region 19 and the distal end region 18 together in a static relationship.

Figure 2:
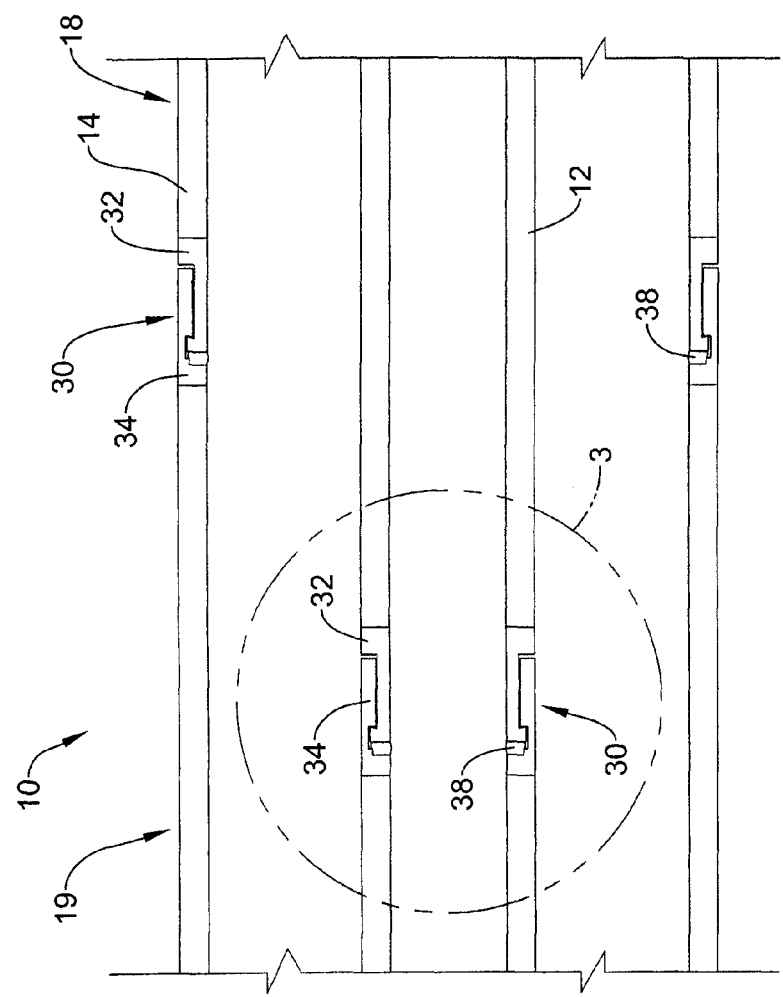
FIG. 2 is an enlarged view of a section of the embodiment shown in FIG. 1.

As is shown in FIG. 2, each seal mechanism is comprised of two radially overlapping bushing components: a first or inner component 32, and a second or outer component 34. Each component 32 and 34 is also engaged to the respective proximal region 19 or distal region 18 of the assembly 10. It should be noted that the particular arrangement and orientation of the components shown in the present embodiment is but one example of any number of possible configurations. It should be recognized that the position and orientation of the components 32 and 34, relative to one another and to the regions of the assembly can be modified and reconfigured as desired. For example the "outer" component 34 can be made to extend from the proximal region 19, rather than the distal region 18, and the "inner" component 32 can be similarly repositioned. Likewise, the "inner" and "outer" relationship of the components can be rearranged and configured as desired.

In some embodiments, two or more seals 30 may be placed along the catheter shaft to decrease rotational friction of the distal end portion otherwise affected by a real-world non-zero friction potential in a single seal configuration.

Regardless of which configuration is selected, in all embodiments it is desirable to provide the components 32 and 34 with a "bayonet" lock configuration, such as is shown in FIG. 2, wherein the components 32 and 34 effectively interlock so that longitudinal separation of the catheter regions is prevented regardless of the activation state of the seals 30. A bayonet lock type mechanism is known and understood and alternative configurations of the seal components may be used other than that which is shown. Such alternative configurations are considered to be within the scope of the present invention.

While the arrangement and configuration of the seal components may be varied, it is necessary that a given seal 30, provide the assembly 10 with the ability to allow the distal end region 18 to be rotated relative to the proximal region 19 while the assembly is within the confines of a body lumen or vessel 100, such as is shown in FIG. 1.

Figure 3:
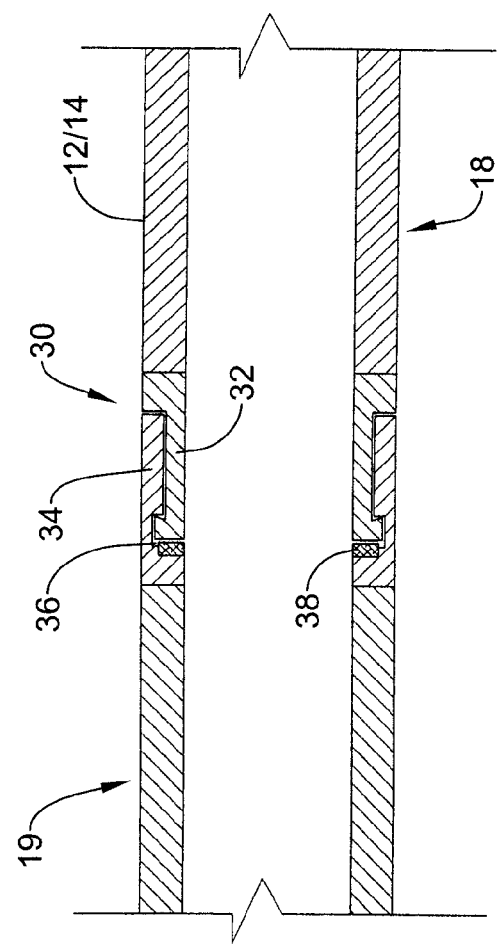
FIG. 3 is an enlarged view of the rotational seal mechanism shown in FIG. 2, wherein the seal mechanism is shown in the rotatable or non-activated state.
Figure 4:
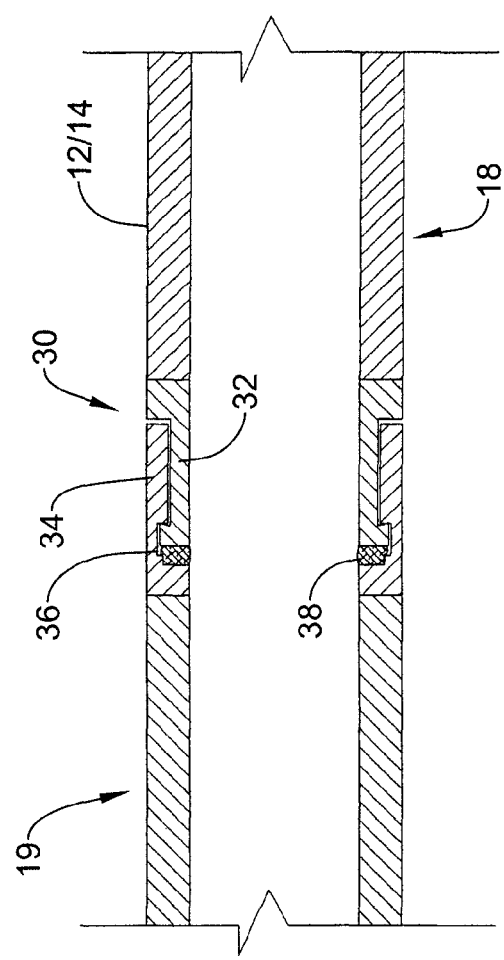
FIG. 4 is an enlarged view of the rotational seal mechanism shown in FIG. 2, wherein the seal mechanism is shown in the non-rotatable or activated state.

In at least one embodiment, such as in the example shown in FIGS. 3 and 4, a seal 30 is provided with at least two activation states. In the "non-activated" state, such is shown in FIG. 3, the components 32 and 34 of the seal have somewhat of a reduced friction region, or gap 36 therebetween; whereas when the seal 30 is activated, such as is shown in FIG. 4, the components 32 and 34 are forced together to prevent pressure leakage, but preventing free rotation of the distal end region 18 at the same time.

Figure 7:
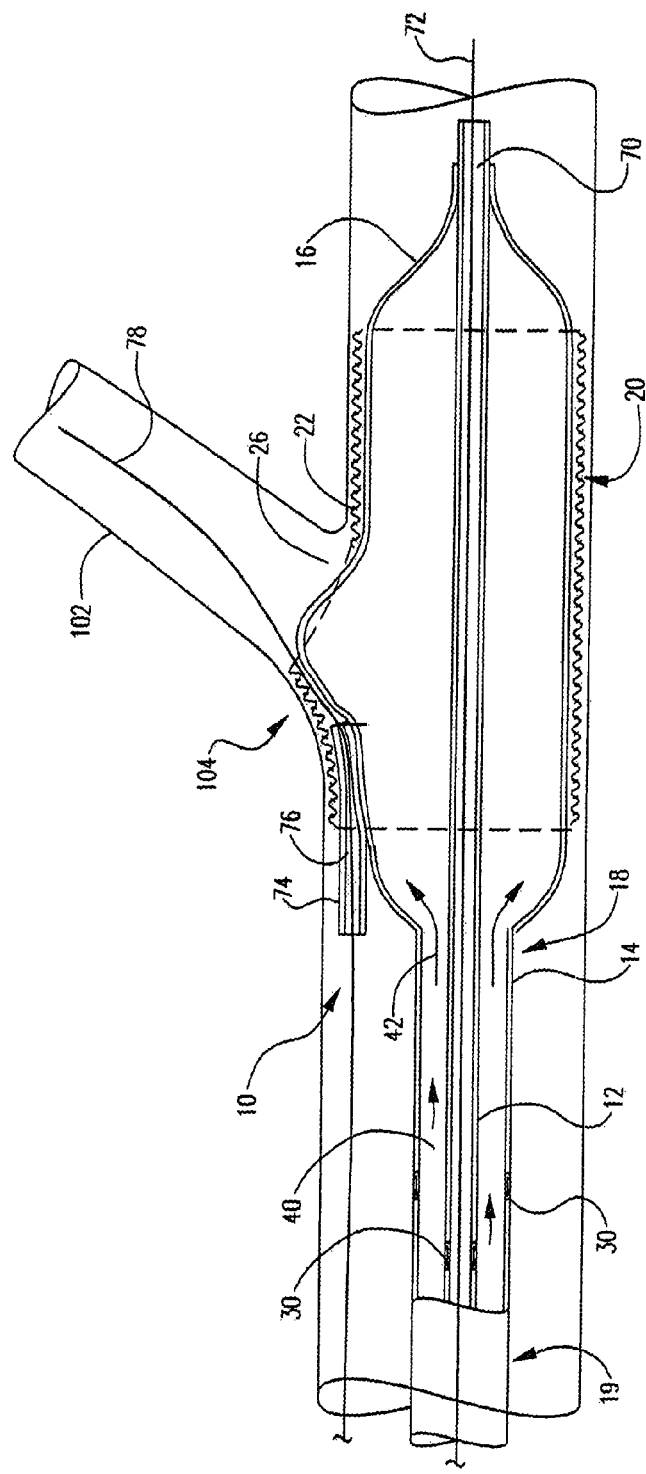
FIG. 7 is a longitudinal side perspective view of the embodiment shown in FIG. 1 wherein a stent disposed about the distal end region of the catheter assembly is shown being deployed.

In at least one embodiment activation of the seal 30 is a function of the pressurization of the inflation lumen 40, which is defined by the inner catheter shaft 12 and the outer catheter shaft 14 such as is shown in FIG. 7. Pressurization occurs when a fluid, represented by arrow 42 is passed through the lumen 40 and into the balloon 16. As the pressurized fluid 42 is injected into the balloon 16 the balloon 16 will expand to deliver the stent 20 to the bifurcation 104 in the manner shown in FIGS. 7 and 8.

As the pressure within the balloon 16 and lumen 40 builds the inner component of the seal 30 will be pushed outward toward the outer component. As the components are pushed together the gap will close and thus the seal will be "activated" thereby preventing rotation of the distal end region 18 relative to the proximal region 19. In an embodiment wherein activation is caused by pressurization, the outer component 34 is preferably constructed of a material or materials that is harder and/or more rigid than that of the inner component 32, in order to allow the inner component 32 to press against the outer component without adversely affecting the outer diameter of the catheter shaft 12/14 in the region of the seal(s) 30.

In some embodiments activation and/or deactivation of the seals 30 is not necessarily dependent on the pressurization of the inflation lumen 40. In at least one embodiment, an example of which is shown in FIGS. 2-4, one or both of the components 32 and 34 of a given seal 30 include at least one layer 38 of EAP material. One or more layers 38 of EAP material may be affixed to one or both of the components 32 and/or 34 within the gap 36, such that when activated by exposure to a low voltage electric current the EAP layer 38 will expand to close the gap and push the components 32 and 34 against one another, thereby stopping the rotation of the distal region 18. FIG. 3 illustrates a seal 30 wherein the layer 38 is shown before activation, while FIG. 4 shows the same seal 30 with the layer 38 shown activated and expanded such that the gap 36 is effectively "sealed".

Activation of the EAP layer 38 may be by any of a variety of mechanisms. For example the proximal region 19 of the catheter 10 may include one or more electrically conductive elements, the inflation fluid 42 and/or bodily fluids (not shown) may alternatively or additionally be utilized to transmit a low voltage electric current to the EAP layer 38 as desired. In some embodiments the seal 30 may be further equipped with an electrical current producing element directly that may triggered external to the patient by radio, ultrasound, or any desired transmittable signal.

EAP material suitable for the construction of layer 38 and/or the seal 30 or portions thereof, may include but is not limited to: Poly-pyrrole (PPY), Poly-Aniline (PAni), Poly-Thiofene (PTH), Poly-Paraphenylene Vinylene (PPV), Nafion, or any other ionic electro-active polymer that is considered to have low voltage, low to moderate speed, high stress (up to 500 MPa), characteristics.

EAP materials and some of their notable characteristics are described in an article entitled *Electro-Active Polymer Actua-*

*tors for Planetary Applications* by Y. Bar-Cohen et al. and published in Paper No. 3669-05 of the Proceedings of SPIE Annual International Symposium on Smart Structures and Materials, March 1999, Newport Beach, Calif. SPIE Copyright 1999, the entire contents of which being incorporated herein by reference.

Figure 5:
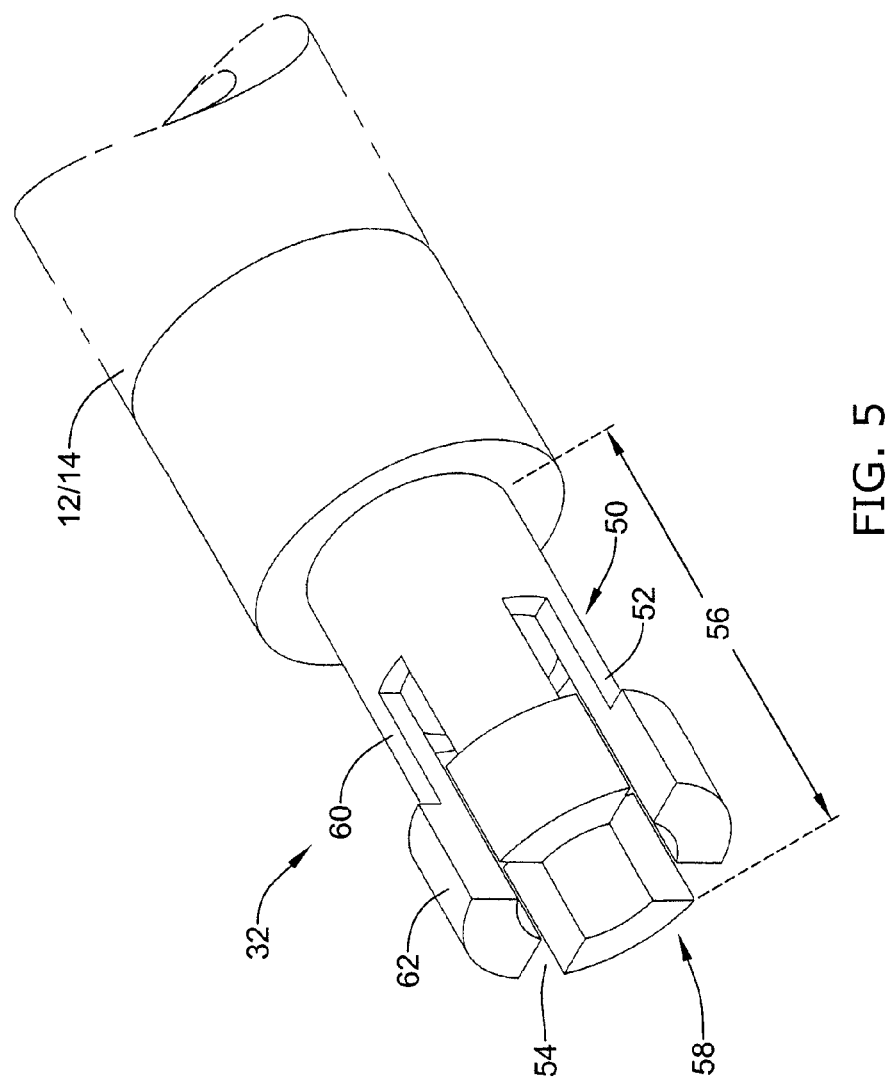
FIG. 5 is a partial enlarged perspective view of an embodiment of the rotational seal mechanism.
Figure 6:
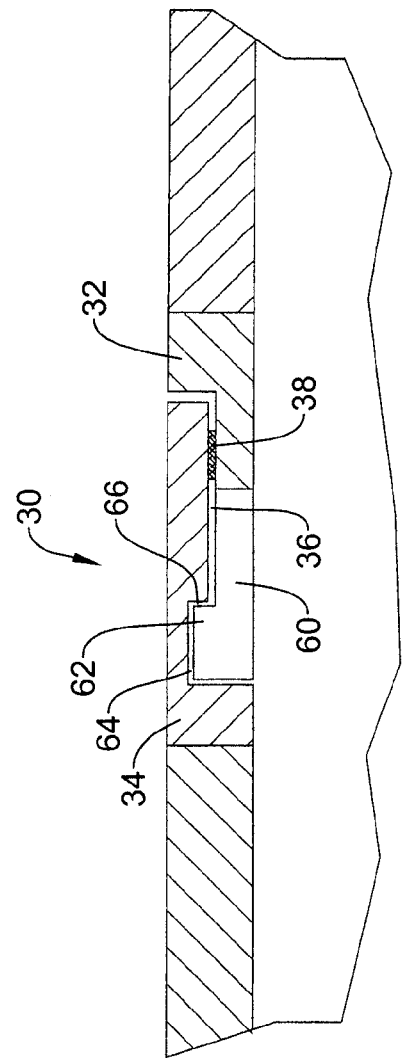
FIG. 6 is a partial longitudinal cross-sectional view of the embodiment shown in FIG. 5

In at least one embodiment the seal 30 is configured in the manner shown in FIGS. 5 and 6. In the embodiment shown, the inner component 32 comprises a pin 50 which defines a plurality of tabs 52, each of which are separated by an elongate opening or slots 54. The slots may be of any length, but in the embodiment shown each slot 54 extends approximately half the length 56 of the pin 50 from its end 58.

Each of the tabs 52 include an arm region 60 and an engagement region 62. The engagement region 62 is positioned at the end of the arm region 60 and is constructed and arranged to have a complementary fit into a recess 64 of the outer seal component 34. The recess 64 is defined by an engagement collar or ridge 66 positioned on the end of the outer component 34 such as in the manner shown in FIG. 6.

In the non-activated state the ridge 66 and the engagement region 62 interact to allow rotation of the distal end region 18 relative to the proximal region 19 of the catheter 10 (via the gap 36), but prevents longitudinal separation of the distal end region 18 from the proximal region 19.

In at least one embodiment the pin 50 is at least partially constructed from spring steel, nitinol, polycarbonate, or similarly hard substances, so that the engagement region 62 will tend to "pop" up into the recess 64 when the regions 18 and 19 are brought together during assembly.

In at least one embodiment friction between the seal components 32 and 34 may be reduced by applying a biocompatible lubricant between the components 32 and 34 within the gap 36.

As shown in FIG. 6 the use of one or more layers of EAP material may be used to seal the components 32 and 34 together in the manner previously described. Prior to activation of the seal 30 the EAP layer 38 may be positioned anywhere within the gap 36, but is preferably adjacent to the slots such that the quantity of EAP material necessary to effectuate the seal is minimized (i.e. it is not necessary to fill in all of the slots 54 but rather only a portion of the gap 36 as shown).

In the various embodiments described herein the catheter assembly 10 may be a fixed wire catheter or any other catheter design. In the embodiment depicted in FIGS. 1 and 7 for example the catheter is an over the wire design wherein the inner shaft 12 defines a primary guidewire lumen 70 along which a primary guidewire 72 may be advanced.

In some embodiments, such as are illustrated in FIGS. 1 and 7, the catheter assembly 10 is provided with a mechanism for aligning the distal end region 18 with the secondary vessel 102 of the bifurcation 104. In the embodiment shown, such a mechanism is comprised of a secondary guidewire housing 74.

Housing 74 may be comprised of an tubular member which defines a secondary guidewire lumen 76 through which a secondary guidewire 78 may be advanced. The housing 74 is engaged to the balloon 16 or defined by the balloon wall as desired. The housing 74 may be comprised of one or more tubular members to provide a desired degree of flexibility for traversing the tortuous confines of body vessel(s). Housing 74 may be constructed of any of a wide variety of materials including metal(s), polymer(s), natural rubber, silicone, multilayer materials, Pebax, HDPE, etc.

When the stent 20 is properly positioned on the balloon 16, such as in the manner depicted in FIGS. 1 and 7, at least a portion of the stent 20 is also disposed about at least a portion of the secondary guidewire housing 74. When the stent is thusly positioned about the balloon 16 and the housing 74, in some embodiments a portion of the housing 80 and/or the secondary guidewire 78 may be configured to extend distally through the secondary opening 26 of the stent 20.

In some embodiments, the secondary guidewire 78 is merely slid between the balloon 16 and the stent 20 without the use of a housing 74. In some embodiments, where the stent 20 is to be positioned substantially proximal to a side branch of a vessel bifurcation, the guidewire 78 and/or housing 74 may be configured to extend under the entire length of the stent 20.

In operation, the secondary guidewire 78 is initially advanced through the vessel 100 and into a side branch 102 of the bifurcation 104. By advancing the catheter assembly 10 along the secondary guidewire 78 and the primary guidewire 72 in the manner shown in FIG. 1, the entire distal end region 18, including the balloon 16 and stent 20 will be rotated to align the secondary opening 26 of the stent 20 with the side branch vessel 102.

Figure 8:
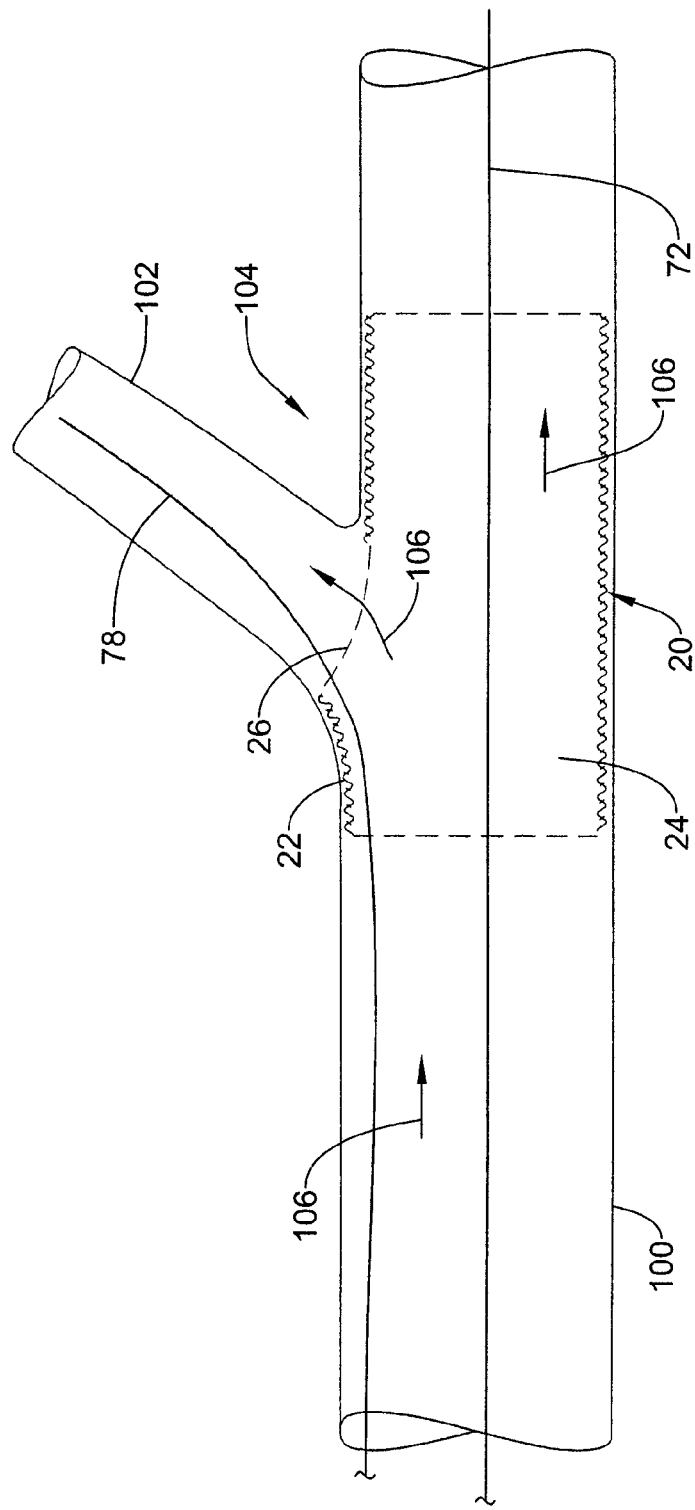
FIG. 8 is a longitudinal side perspective view of the embodiment shown in FIG. 7 shown following deployment of the stent at the vessel bifurcation and withdrawal of the catheter assembly.

Once properly positioned in this manner the seals 30 are activated and the balloon 16 is expanded to deliver the stent 20 such as in the manner depicted in FIGS. 7 and 8.

Once the stent 20 is delivered the balloon 16 is deflated and the assembly is withdrawn from the vessel 100.

A therapeutic agent may be placed on the stent and/or other portion of the assembly 10 in the form of a coating. Often the coating includes at least one therapeutic agent and at least one polymer.

A therapeutic agent may be a drug or other pharmaceutical product such as non-genetic agents, genetic agents, cellular material, etc. Some examples of suitable non-genetic therapeutic agents include but are not limited to: antithrombogenic agents such as heparin, heparin derivatives, vascular cell growth promoters, growth factor inhibitors, Paclitaxel, etc. Where an agent includes a genetic therapeutic agent, such a genetic agent may include but is not limited to: DNA, RNA and their respective derivatives and/or components; hedgehog proteins, etc. Where a therapeutic agent includes cellular material, the cellular material may include but is not limited to: cells of human origin and/or non-human origin as well as their respective components and/or derivatives thereof. Where the therapeutic agent includes a polymer agent, the polymer agent may be a polystyrene-polyisobutylene-polystyrene triblock copolymer (SIBS), polyethylene oxide, silicone rubber and/or any other suitable substrate.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

With this description, those skilled in the art may recognize other equivalents to the specific embodiment described herein. Such equivalents are intended to be encompassed by the claims attached hereto.

The invention claimed is:

1. A catheter assembly comprising:
   a catheter shaft, the catheter shaft having a proximal region, a distal region, and a rotational seal therebetween,
   the rotational seal comprising a first component and a second component, the first component fixedly engaged to the proximal region of the catheter shaft, the second component fixedly engaged to the distal region of the catheter shaft, the first component and the second component being overlappingly engaged, and
   the rotational seal having an activated state and a non-activated state, in the non-activated state the first component and the second component being separated by a gap which provides for the distal region of the catheter shaft to be rotatable relative to the proximal region of the catheter shaft, in the activated state the first component and the second component being sealingly engaged together such that the distal region is made static relative to the proximal region;
   wherein a portion of the first component of the rotational seal is engaged with a portion of the second component of the rotational seal in both the activated and non-activated states to prevent axial separation of the proximal region of the catheter shaft from the distal region of the catheter shaft.

2. The catheter assembly of claim 1 wherein the rotational seal further comprises a layer of electro-active polymer (EAP) material, in the non-activated state the layer of EAP material being fixedly engaged to one of the first and second components, a portion of the layer of EAP material defining at least a portion of the gap, in the activated state the EAP layer expanding in volume to sealingly engage the other component.

3. The catheter assembly of claim 2 wherein in the activated state the layer of EAP material expands in volume by about 1 to about 30 percent.

4. The catheter assembly of claim 2 wherein the EAP material is selected from at least one material of the group consisting of: Poly-pyrrole (PPY), Poly-Aniline (PAni), Poly-Thiofene (PTH), Poly-Paraphenylene Vinylene (PPV), Nafion, and any combination thereof.

5. The catheter assembly of claim 1 wherein the first component and the second component are overlappingly arranged in a bayonet lock configuration.

6. The catheter assembly of claim 1 wherein the second component is constructed of a material that is harder than the first component.

7. The catheter assembly of claim 1 wherein the first component comprises a pin, the pin having a plurality of arms, each of the arms separated by a slot, wherein the slot is defined by the adjacent arms, each of the arms having an engagement portion, each of the engagement portions being at least partially positioned within a recess defined by the second component.

8. The catheter assembly of claim 1 wherein the catheter shaft defines a first guidewire lumen for passage of a first guidewire therethrough, the first guidewire lumen extending through the proximal region and the distal region.

9. The catheter assembly of claim 1 wherein the distal region comprises an expandable balloon.

10. The catheter assembly of claim 9 further comprises a secondary guidewire housing, the secondary guidewire housing being engaged to the balloon and defining a secondary guidewire lumen for passage of a secondary guidewire therethrough.

11. The catheter assembly of claim 9 wherein the catheter shaft defines an inner shaft and an outer shaft, the inner shaft having an inner shaft rotational seal between a proximal region of the inner shaft and a distal region of the inner shaft, the outer shaft having an outer shaft rotational seal between a proximal region of the outer shaft and the distal region of the outer shaft.

12. The catheter assembly of claim 11 wherein the inner shaft and the outer shaft define an inflation lumen, the inflation lumen in fluid communication with the balloon.

13. A system for delivery of a stent to a vessel bifurcation comprising:
    a catheter, the catheter comprising a catheter shaft, the catheter shaft having a proximal region, a distal region, and a rotational seal therebetween, at least a portion of the distal region comprising an expandable balloon,
    the rotational seal comprising a first component and a second component, the first component fixedly engaged to the proximal region of the catheter shaft, the second component fixedly engaged to the distal region of the catheter shaft, the first component having a first reduced diameter portion, the second component having a first engagement portion, the first engagement portion being radially aligned with the first reduced diameter portion,
    the rotational seal having an activated state and a non-activated state, in the non-activated state the first component and the second component being separated by a gap which provides for the distal region of the catheter shaft to be rotatable relative to the proximal region of the catheter shaft, in the activated state at least a portion of the first component and the second component being sealingly engaged together such that the distal region is made static relative to the proximal region;
    wherein the first component has a second engagement portion and the second component has a second reduced diameter portion, the second engagement portion being radially aligned with the second reduced diameter portion to provide engagement of the first and second engagement portions in both the activated and non-activated states of the rotational seal to prevent axial separation of the proximal region of the catheter shaft from the distal region of the catheter shaft; and
    a stent, the stent being expandable from a pre-delivery state to a delivery state, wherein in the delivery state the stent has a greater diameter than in the pre-delivery state, in the pre-delivery state the stent being disposed about at least a portion of the balloon.

14. The system of claim 13 wherein the catheter shaft defines a first guidewire lumen for passage of a first guidewire therethrough, the first guidewire lumen extending through the proximal region and the distal region.

15. The system of claim 13 further comprising a secondary guidewire housing, the secondary guidewire housing being engaged to the balloon and defining a secondary guidewire lumen for passage of a secondary guidewire lumen therethrough, the stent being at least partially disposed about the secondary guidewire housing.

16. A method of treating a vessel bifurcation comprising the steps of:
- advancing a first guidewire through a first vessel, such that the first guidewire extends proximally beyond a bifurcation of the first vessel and a second vessel;
- advancing a second guidewire through the first vessel to the bifurcation and into the second vessel;
- providing a stent delivery system, the system comprising:
  - a catheter, the catheter having a catheter shaft, the catheter shaft having a proximal region, a distal region, and a rotational seal therebetween, at least a portion of the distal region comprising an expandable balloon, the catheter shaft defining a first guidewire lumen for passage of the first guidewire therethrough, the first guidewire lumen extending through the proximal region and the distal region,
  - a secondary guidewire housing being engaged to the balloon, the secondary guidewire housing defining a secondary guidewire lumen for passage of the secondary guidewire lumen therethrough, the stent being at least partially disposed about the secondary guidewire housing,
  - the rotational seal comprising a first component and a second component, the first component fixedly engaged to a distal end of the proximal region of the catheter shaft, the second component fixedly engaged to a proximal end of the distal region of the catheter shaft, the first component and the second component being overlappingly engaged,
  - the rotational seal having an activated state and a non-activated state, in the non-activated state, at least a first portion of the first component and at least a first portion of the second component being separated by a gap which provides for the distal region of the catheter shaft to be rotatable relative to the proximal region of the catheter shaft, in the activated state at least the first portion of the first component and the second component being sealingly engaged together such that the distal region is made static relative to the proximal region;
  - wherein a second portion of the first component of the rotational seal is engaged with a second portion of the second component of the rotational seal in both the activated and non-activated states to prevent axial separation of the proximal region of the catheter shaft from the distal region of the catheter shaft; and
  - a stent, the stent being expandable from a pre-delivery state to a delivery state, wherein in the delivery state the stent has a greater diameter than in the pre-delivery state, in the pre-delivery state the stent being disposed about at least a portion of the balloon, the stent defining a secondary opening for passage of the secondary guidewire therethrough;
- advancing the stent delivery system along the first guidewire and the second guidewire through the first vessel, wherein the rotational seal is in the non-activated state;
- rotationally aligning the distal region of the catheter shaft such that the secondary opening of the stent is in communication with the second vessel;
- actuating the rotational seal from the non-activated state to the activated state; and
- expanding the balloon to deliver the stent.

* * * * *

UNITED STATES PATENT AND TRADEMARK OFFICE
CERTIFICATE OF CORRECTION

PATENT NO.         : 8,353,944 B2                                    Page 1 of 1
APPLICATION NO.    : 11/079756
DATED              : January 15, 2013
INVENTOR(S)        : Jan Weber et al.

It is certified that error appears in the above-identified patent and that said Letters Patent is hereby corrected as shown below:

In the Specifications:

Column 8, Line 34:

Delete "antithrombogenic" and insert -- anti-thrombogenic --.

Signed and Sealed this
Fourth Day of June, 2013

Teresa Stanek Rea
*Acting Director of the United States Patent and Trademark Office*